US012039095B2

(12) United States Patent
O'Connor et al.

(10) Patent No.: US 12,039,095 B2
(45) Date of Patent: Jul. 16, 2024

(54) BREATH-OPERATED INTERFACE DEVICE AND DISPOSABLE MODULE FOR SAME

(71) Applicant: Curbell Medical Products, Inc., Orchard Park, NY (US)

(72) Inventors: Thomas O'Connor, Orchard Park, NY (US); Joel Jusiak, Orchard Park, NY (US)

(73) Assignee: Curbell Medical Products, Inc., Orchard Park, NY (US)

( * ) Notice: Subject to any disclaimer, the term of this patent is extended or adjusted under 35 U.S.C. 154(b) by 213 days.

(21) Appl. No.: 17/700,209

(22) Filed: Mar. 21, 2022

(65) Prior Publication Data

US 2022/0300068 A1   Sep. 22, 2022

Related U.S. Application Data

(60) Provisional application No. 63/163,778, filed on Mar. 19, 2021.

(51) Int. Cl.
*H01H 3/24* (2006.01)
*A61B 5/00* (2006.01)
*G06F 3/01* (2006.01)

(52) U.S. Cl.
CPC ............ *G06F 3/011* (2013.01); *A61B 5/7475* (2013.01); *H01H 3/24* (2013.01)

(58) Field of Classification Search
CPC ........ H01H 3/24; H01H 35/24; A61B 5/7475; G06F 3/011
See application file for complete search history.

(56) References Cited

U.S. PATENT DOCUMENTS 5,126,731 A * 6/1992 Cromer, Jr. ............... A61F 4/00
340/4.11

* cited by examiner

*Primary Examiner* — Benyam Haile
(74) *Attorney, Agent, or Firm* — Hodgson Russ LLP

(57) ABSTRACT

A breath-operated interface device having a disposable module and a base. The disposable module having a breath tube with an inlet. A first pressure differential switch is in pneumatic communication with the breath tube and configured to be actuated by a change in pressure in the breath tube. A first signal coupler of the disposable module is in electrical communication with the first pressure differential switch to receive a signal according to an actuation state of the first pressure differential switch. The device may also include a base with a second signal coupler, where the second signal coupler is configured to detachably electrically connect with the first signal coupler of the disposable module. The base also includes a station interconnect configured to interface with an external system, such as, for example, a nurse call system.

15 Claims, 7 Drawing Sheets

BREATH-OPERATED INTERFACE DEVICE AND DISPOSABLE MODULE FOR SAME

CROSS-REFERENCE TO RELATED APPLICATIONS

This application claims priority to U.S. Provisional Application No. 63/163,778, filed on Mar. 19, 2021, the disclosure of which is incorporated herein by reference.

FIELD OF THE DISCLOSURE

The present disclosure relates to devices controlled using the breath of an individual.

BACKGROUND OF THE DISCLOSURE

Breath-operated interface devices (so-called "sip-and-puff" devices) are used by individuals having limited motor control. Such devices are useful for interfacing with various equipment—e.g., wheelchairs, computers, entertainment/information systems, nurse call systems, etc. Sip-and-puff devices are quickly contaminated through normal use because of the individual placing a portion of the device into their mouth and breathing into a breath tube. There is a need for an economical breath-operated interface device having improved ability for hygienic use.

BRIEF SUMMARY OF THE DISCLOSURE

The present disclosure may be embodied as a breath-operated interface device. The device includes a disposable module having a breath tube with an inlet. A first pressure differential switch is in pneumatic communication with the breath tube. The first pressure differential switch is configured to be actuated by a change in pressure in the breath tube. For example, the first pressure differential switch may be configured to be actuated by an increase in pressure in the breath tube. In another example, the first pressure differential switch is configured to be actuated by a decrease in pressure in the breath tube. In some embodiments, the first pressure differential switch has a first actuation state actuated by an increase in pressure in the breath tube and a second actuation state actuated by a decrease in pressure in the breath tube.

The disposable module includes a first signal coupler in electrical communication with the first pressure differential switch. The first signal coupler receives a signal according to an actuation state of the first pressure differential switch. In some embodiments, the first pressure differential switch is configured to be actuated by an increase in pressure in the breath tube, and the disposable module further includes a second pressure differential switch in pneumatic communication with the breath tube and configured to be actuated by a decrease in pressure in the breath tube. In such an embodiment, the first signal coupler may also be in electrical communication with the second pressure differential switch to receive a signal according to an actuation state of the second pressure differential switch.

The device also includes a base with a second signal coupler. The second signal coupler is configured to detachably electrically connect with the first signal coupler of the disposable module. For example, the first signal coupler may be a 3.5 mm plug and the second signal coupler may be a 3.5 mm jack configured to couple with the 3.5 mm plug. The base also includes a station interconnect configured to interface with an external system. For example, the station interconnect may be configured to interface with a nurse call system. Such an interface may be via an 8-pin DIN connector, a ¼" plug, a double ¼" plug, and/or an RJ45 connector. The station interconnect may further include a signal circuit.

The disposable module may further have a body to which the first pressure differential switch is mounted. The body may be a housing and the first pressure differential switch may be contained within the housing. In some embodiments, at least a portion of the first signal coupler is external to the housing.

The base may include a clamp for attachment to an object. The base may be configured for removable attachment of the disposable module (e.g., the body of the disposable module). In some embodiments, the base includes an arm configured for attachment of the breath tube at one or more locations along a length of the arm.

In another aspect, the present disclosure may be embodied as a disposable module having a breath tube with an inlet. A first pressure differential switch is in pneumatic communication with the breath tube. The first pressure differential switch is configured to be actuated by a change in pressure in the breath tube. For example, the first pressure differential switch may be configured to be actuated by an increase in pressure in the breath tube. In another example, the first pressure differential switch is configured to be actuated by a decrease in pressure in the breath tube. In some embodiments, the first pressure differential switch has a first actuation state actuated by an increase in pressure in the breath tube and a second actuation state actuated by a decrease in pressure in the breath tube.

The disposable module includes a first signal coupler in electrical communication with the first pressure differential switch. The first signal coupler receives a signal according to an actuation state of the first pressure differential switch. The first signal coupler is configured for detachable electrical connection with a second signal coupler of a base. The first signal coupler is also configured for communication with a nurse call station by way of the base. The first signal coupler may be, for example, a 3.5 mm plug.

In some embodiments, the first pressure differential switch is configured to be actuated by an increase in pressure in the breath tube, and the disposable module further includes a second pressure differential switch in pneumatic communication with the breath tube and configured to be actuated by a decrease in pressure in the breath tube. In such an embodiment, the first signal coupler may also be in electrical communication with the second pressure differential switch to receive a signal according to an actuation state of the second pressure differential switch.

The disposable module may further have a body to which the first pressure differential switch is mounted. The body may be a housing and the first pressure differential switch may be contained within the housing. In some embodiments, at least a portion of the first signal coupler is external to the housing.

DESCRIPTION OF THE DRAWINGS

For a fuller understanding of the nature and objects of the disclosure, reference should be made to the following detailed description taken in conjunction with the accompanying drawings, in which.

DETAILED DESCRIPTION OF THE DISCLOSURE

The present disclosure provides embodiments of a breath call device to allow physically disabled patients who are incapable of operating a traditional push button call cord or pillow speaker to place a nurse call and control an additional auxiliary through the actuation of a vacuum or pressure activated switch.

Figure 1:
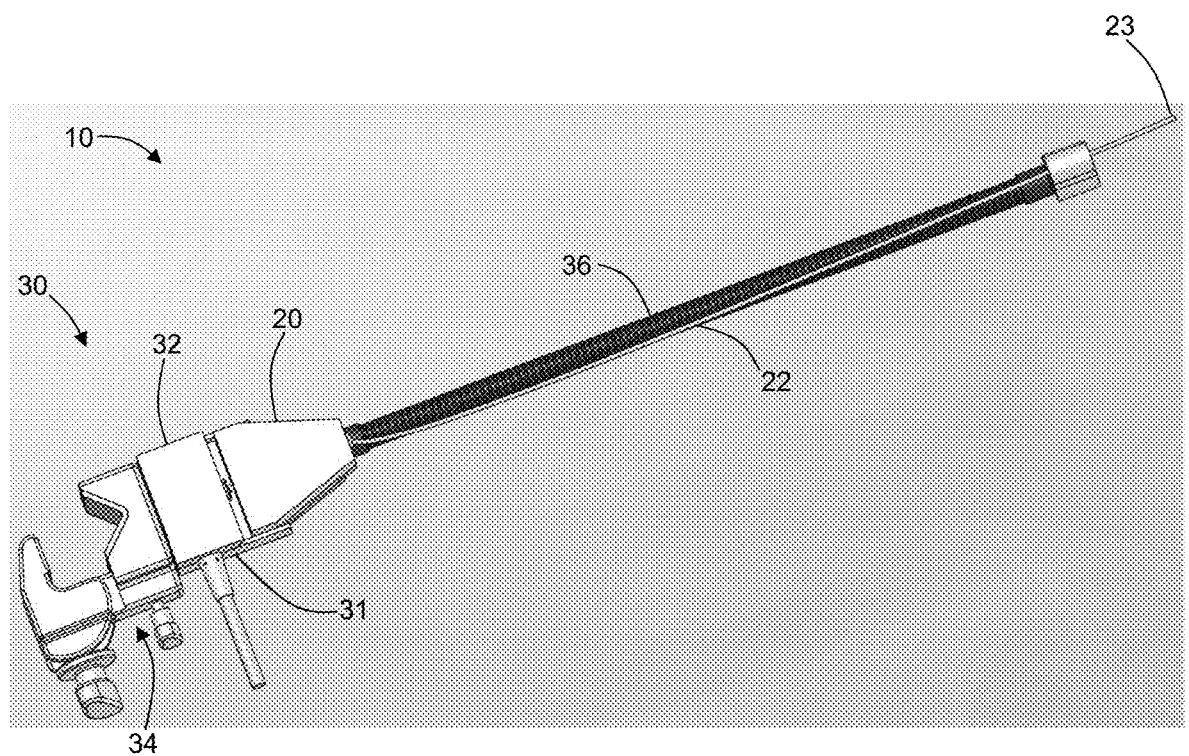
FIG. 1 is a breath-operated interface device according to an embodiment of the present disclosure.
Figure 2:
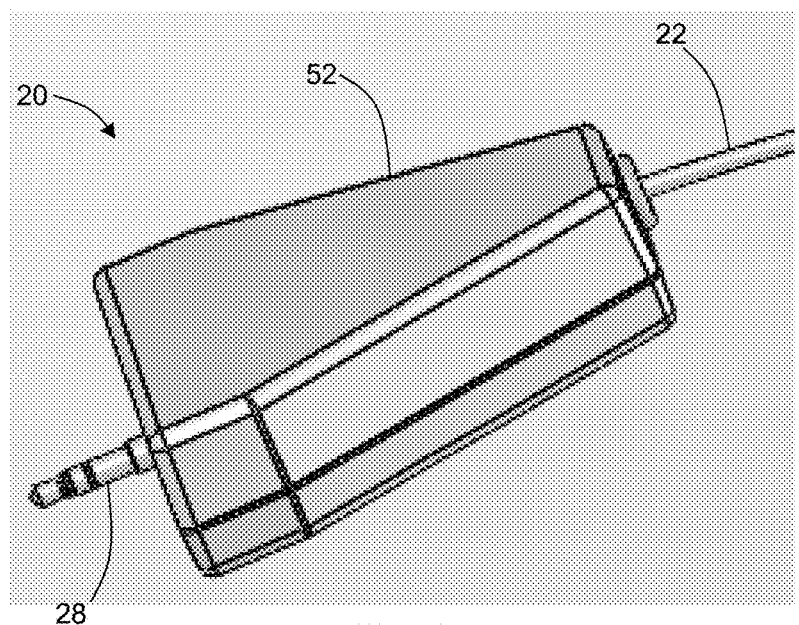
FIG. 2 depicts a portion of a disposable module according to the present disclosure.
Figure 3:
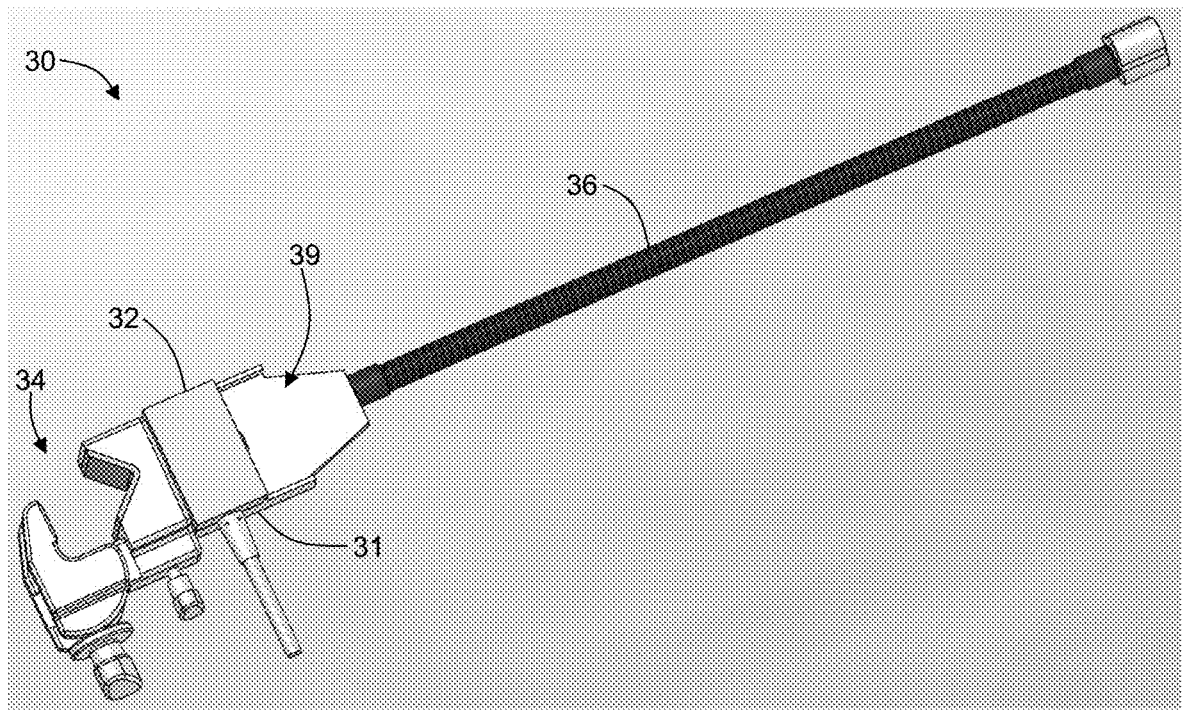
FIG. 3 depicts a base according to an embodiment of the present disclosure.

With reference to FIG. 1, the present disclosure may be embodied as a breath-operated interface device 10 having a disposable module 20 and a base 30. The disposable module may include any components that come into contact with the user during use (e.g., tubing, switches, housing, etc.) and is intended to be used by only one patient. The disposable module 20 has a first pressure differential switch 24. The first pressure differential switch 24 is in pneumatic communication with a breath tube 22 having an inlet 23 (sometimes referred to as a straw). In this way, "puffing" by a user into the inlet 23 will change a pressure in the breath tube 22 thereby actuating the first pressure differential switch 24. In this example, the first pressure differential switch is configured to be actuated by an increase in the pressure within the breath tube (i.e., from the user's "puff"—breathing out). It should be noted that references to relative pressure and/or vacuum herein is generally intended to be relative to an ambient pressure unless expressly stated otherwise. In some embodiments, the first pressure differential switch is configured to be actuated by a decrease in pressure within the breath tube. In this example, a user would actuated the first pressure differential switch by "sipping" on the inlet of the breath tube.

Suitable pressure differential switches may be single pole, single throw; single pole, double throw; double pole, double throw; or other configurations suitable to a particular application. The first pressure differential switch may be a momentary switch configured for normally-open or normally-closed operation. For example, the first pressure differential switch may be configured to cause an open circuit condition between two electrical contacts when the pressure in the breath tube is at the ambient pressure, and then to close the connection between the two electrical contacts when the pressure in the breath tube is increased or lowered (according to the configuration) for the duration of time while the pressure remains elevated or lowered (returning to an open condition once the pressure in the breath tube returns to the ambient).

In another example, the first pressure differential switch has a first actuation state configured to be actuated by an increase in pressure in the breath tube, and the first pressure differential switch has a second actuation state configured to be actuated by a decrease in pressure in the breath tube.

In some embodiments, the device 10 further includes a second pressure differential switch 26 in pneumatic communication with the breath tube 22. For example, the first pressure differential switch may be configured to be actuated by an increase in pressure, and the second pressure differential switch may be configured to be actuated by a decrease in pressure in the breath tube. In this way, "sipping" by a user at the inlet 23 will decrease a pressure (e.g., cause a vacuum) in the breath tube 22, thereby actuating the second pressure differential switch 26. Suitable switches may be single pole, single throw; single pole, double throw; double pole, double throw; or other configurations suitable to a particular application. The second pressure differential switch may be a momentary switch configured for normally-open or normally-closed operation. For example, the second pressure differential switch may be configured to cause an open circuit condition between two electrical contacts when the pressure in the breath tube is at the ambient pressure, and then to close the connection between the two electrical contacts when the pressure in the breath tube is decreased for the duration of time while the pressure remains decreased (returning to an open condition once the pressure in the breath tube returns to the ambient). The second pressure differential switch may be configured the same as or different from the first pressure differential switch. In some embodiments, the first and second pressure differential switches may be share components, such as, for example, a diaphragm responsive to fluid pressures.

Figure 4:
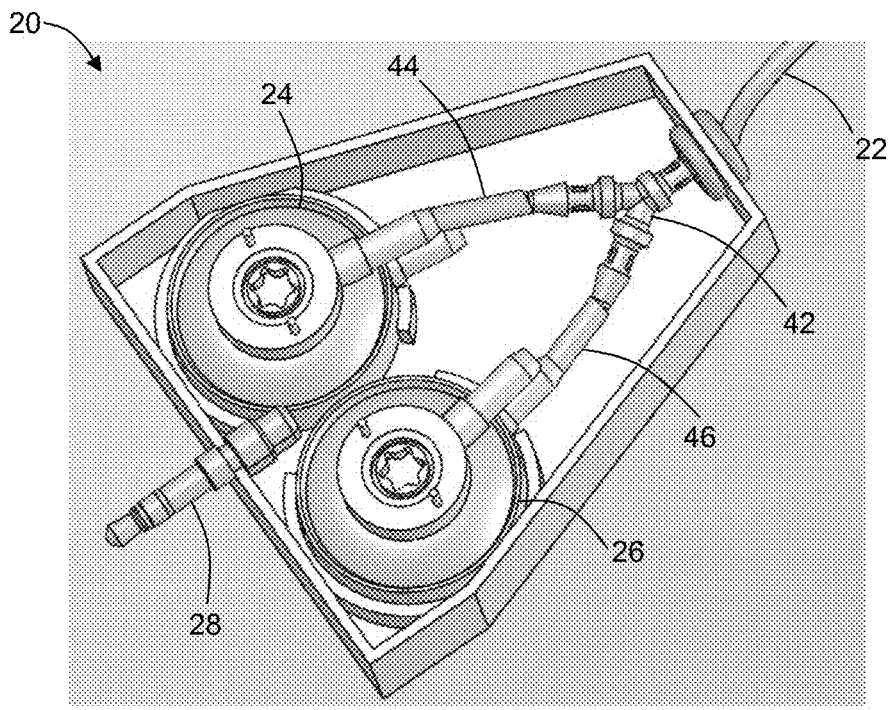
FIG. 4 shows a view of the disposable module of FIG. 2 with a portion of the housing removed to show internal components.

The breath tube 22 may be in pneumatic communication with the first pressure differential switch 24 (and the second differential switch in embodiments having such a switch) by direct connection and/or indirect connection. For example, in embodiments having two separate switches, one or more fittings may be used to branch the breath tube such that a first branch is connected to the first pressure differential switch and a second branch is connected to the second pressure differential switch. FIG. 4 shows a detail of a disposable module 20 showing the breath tube 22 with a 'Y' fitting 42 and connected to the first pressure differential switch 24 by a first branch tube 44 and connected to the second pressure differential switch 26 by a second branch tube 46. Suitable breath tubes may be made from suitable materials such as FDA-listed materials, materials that comply with standards for food contact such as NSF/ANSI Standard 51 (Food Equipment Materials), 3-A certified materials, etc.

The disposable module 20 has a first signal coupler 28 in electrical communication with the first pressure differential switch 24 and/or the second pressure differential switch 26. In this way, the first signal coupler receives one or more "signals" according to an actuation state of the first pressure differential switch and/or an actuation state of the second pressure differential switch. Note that the term "signal" is used to broadly include states of the various switches such as an "open" or "closed" state of the switches, or any other signals which may be applicable according to the type(s) of switches used.

Embodiments of the disposable module 20 may have a body to which the first pressure differential switch 24 and/or the second pressure differential switch 26 may be mounted.

For example, in some embodiments the body is or includes a housing 52 and the first pressure differential switch and the second pressure differential switch are contained within the housing 52. At least a portion of the first signal coupler is external to the housing for connection to a second signal coupler (as further described below).

Figure 5:
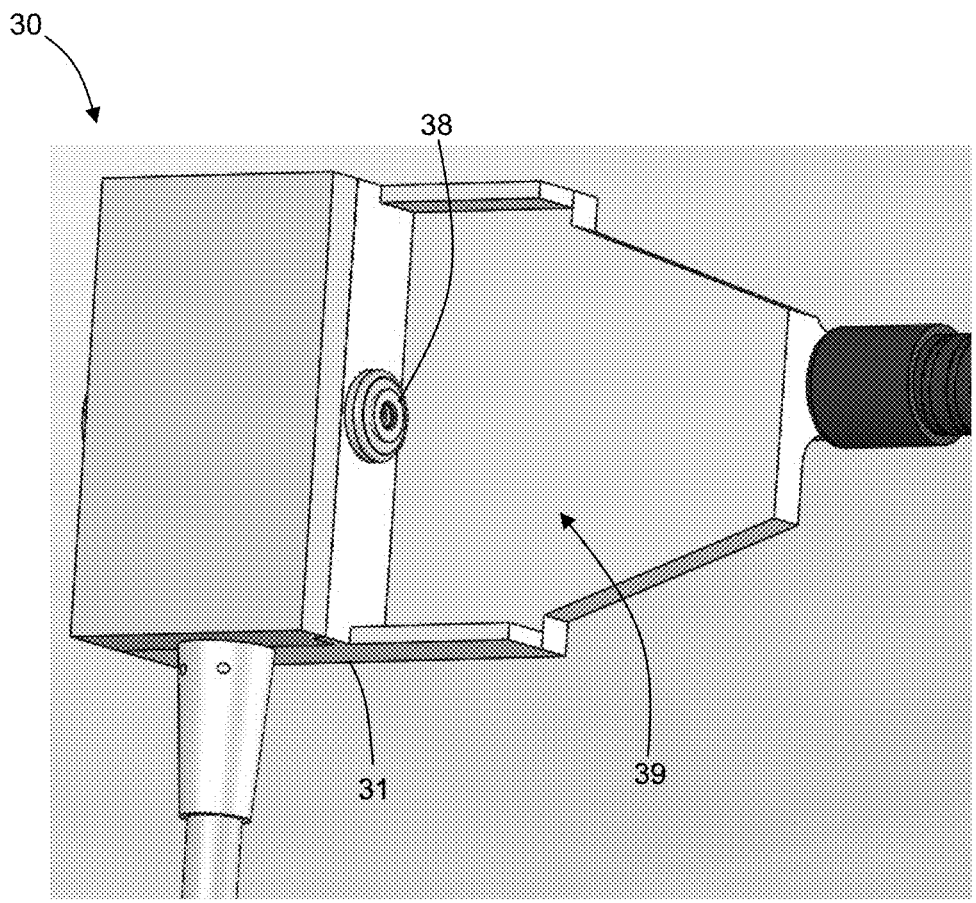
FIG. 5 is a portion of the base of FIG. 3.

The base 30 of the device 10 includes a second signal coupler 38 configured to detachably electrically connect with the first signal coupler 28 of the disposable module 20 (see FIG. 5). The first signal coupler may be, for example, a 3.5 mm plug for connection with a corresponding 3.5 mm jack (the second signal coupler). Other first and second signal coupler configurations may be used such as, for example, ¼" plug/jack, pins, tabs, blades, board-edge connectors, springs, and combinations of these or other configurations. A suitable first and second signal coupler configuration is selected to include at least a number of contacts sufficient for communication with the first pressure differential switch and the second pressure differential switch. For example, a suitable first and second signal coupler configuration may include three contacts to provide a voltage signal to both the first pressure differential switch and the second pressure differential switch and to detect the states of each switch. Fewer contacts or additional contacts may be used as applicable to particular designs.

The base 30 also includes a station interconnect 32 configured to interface an external system such as, for example, a with a nurse call system. In this way, information regarding actuations of the first pressure differential switch and/or the second pressure differential switch can be sent to a nurse call system by way of electrical communication via the first signal coupler connected to the second signal coupler and the station interconnect. It should be noted that the present disclosure is illustrated using the non-limiting example of an external system which is a nurse call system. The scope of the present disclosure is intended to include other external systems, including, for example, room control system, entertainment systems, telecommunication systems, computers, household appliances, etc.

The station interconnect 32 may interface with a nurse call system via an 8-pin DIN connector, a ¼" plug, a double ¼" plug, an RJ45 connector, or any other connector or combinations of connectors. The station interconnect 32 may further comprise a signal circuit to operate the first pressure differential switch and/or the second pressure differential switch. For example, the signal circuit may provide a pressure sense signal to the first pressure differential switch for detection of the open or closed state of the first pressure differential switch. Such a pressure sense signal may be, for example, a positive or negative DC voltage, an AC voltage, a signal having another waveform, etc. Similarly, the signal circuit may provide a vacuum sense signal to the second pressure differential switch for detecting the open or closed state of the second pressure differential switch. The vacuum sense signal can be configured the same or different from the pressure sense signal. In some embodiments, a single signal is provided to both the first pressure differential switch and the second pressure differential switch and the open/closed state may be detected separately. Other configurations for driving the first pressure differential switch and/or the second pressure differential switch may be used as appropriate. Such drive signals may be provided from the signal circuit to the switches by way of the first signal coupler connected to the second signal coupler.

In some embodiments, the signal circuit may condition signals received from the first pressure differential switch and/or the second pressure differential switch. For example, the signal circuit may include one or more debouncing circuits to reduce or eliminate switch bouncing. The signal circuit may include components for other functionality such as, for example, analog-to-digital convertor(s), transceiver (s), filters, amplifiers, etc. The signal circuit may include one or more of a processor, such as a general processing unit, a field-programmable gate array, an application-specific integrated circuit, a digital signal processor, discrete components, etc., or combinations thereof. As such, the signal circuit functionality may be implemented using software, firmware, and/or hardware.

Figure 6:
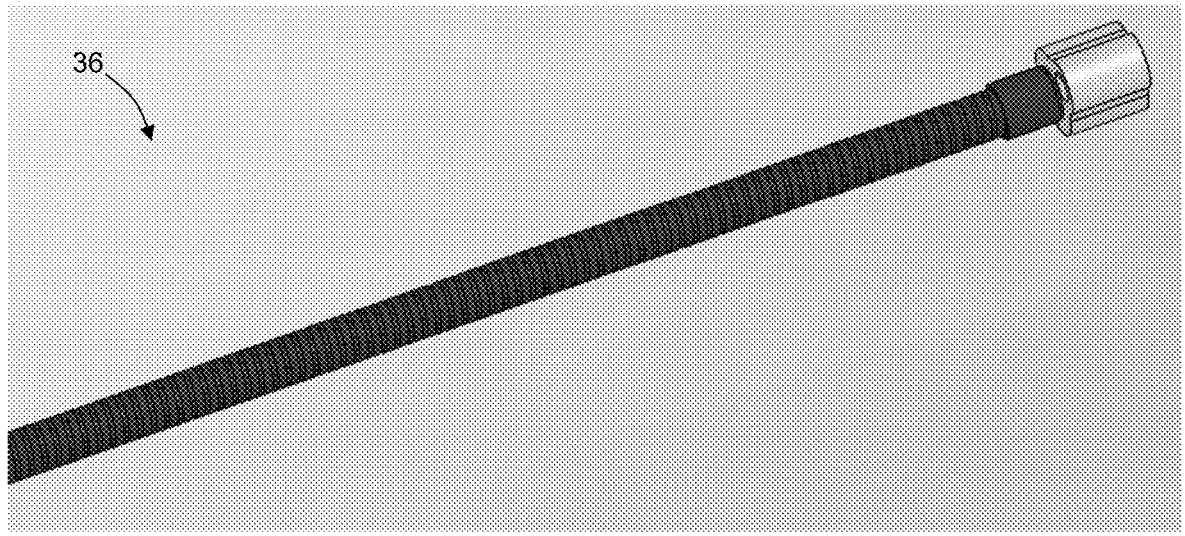
FIG. 6 shows a portion of the gooseneck arm of FIG. 3.

The base 30 may include an arm 36 configured for attachment of the breath tube at one or more locations along a length of the arm (see, e.g., FIG. 6). The arm 36 may be an articulating arm, such as a gooseneck, a jointed arm, bendable wire, etc. or combinations. The breath tube 22 may be attached to the arm using one or more clips, straps, bosses, etc. or combinations.

Figure 7:
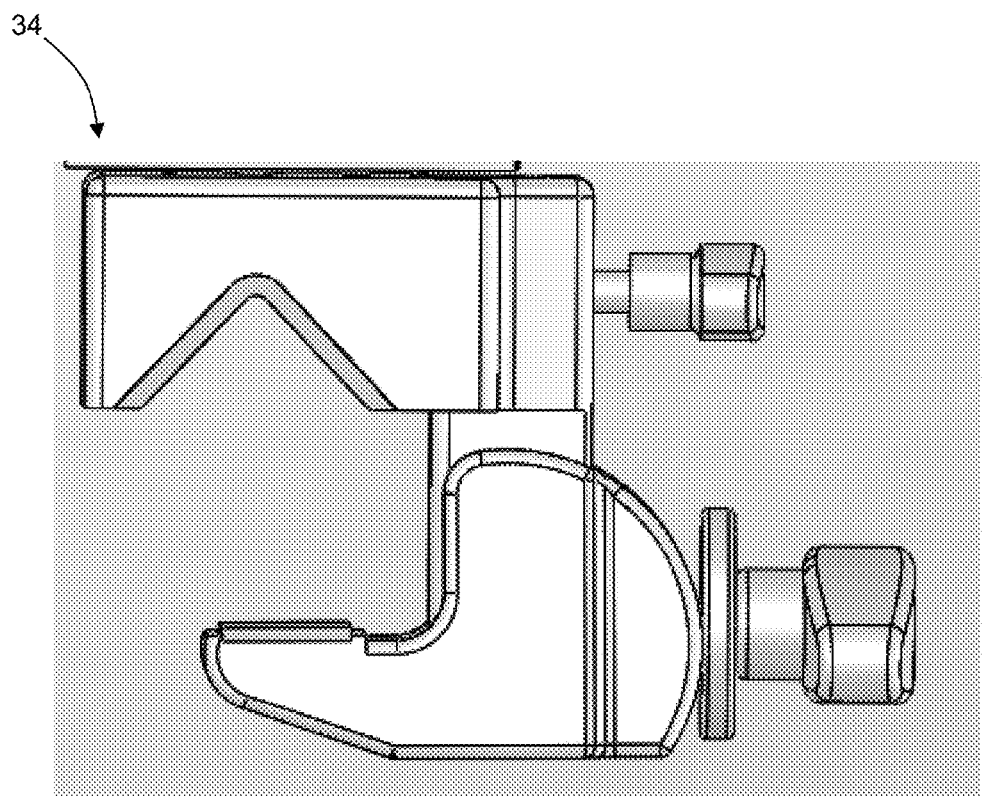
FIG. 7 shows the clamp of FIG. 3.

The base 30 may include a clamp 34 for attachment to an environmental object (see, e.g., FIG. 7). For example, the clamp may allow the base to be attached to a wheelchair, bed rail, table, chair, etc.

The base 30 may include a frame 31 to which other components are mounted (e.g., signal circuit, arm, station interconnect, clamp, etc.) The frame 31 may be configured for removable attachment of the body of the disposable module 20. For example, FIG. 5 depicts a frame 31 having a receiver 39 in which the body of the disposable module is located when attached (thereby coupling the first signal coupler and the second signal coupler). In another example, the frame of the base and the body of the disposable module may attach magnetically. Other embodiments, may use latches, straps, tabs, fasteners, etc. or combinations to provide attachment of the disposable module to the base and allowing removal (e.g., when readying a device for use by a second individual). In some embodiments, the base and the disposable module are attached using fasteners (e.g., screws, press-fittings, etc.)

Figure 8:
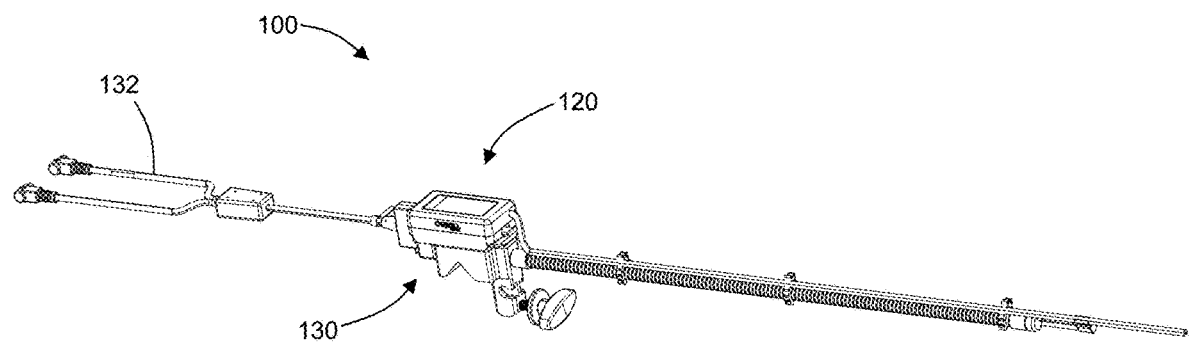
FIG. 8 shows another embodiment of a breath-operated interface device having a interconnect with a double plug.
Figure 9:
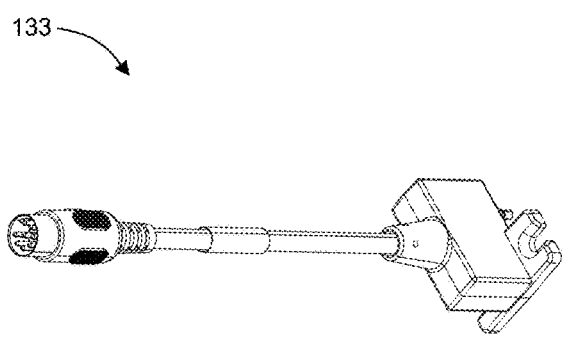
FIG. 9 shows an interconnect having an e-pin DIN connector.
Figure 10A:
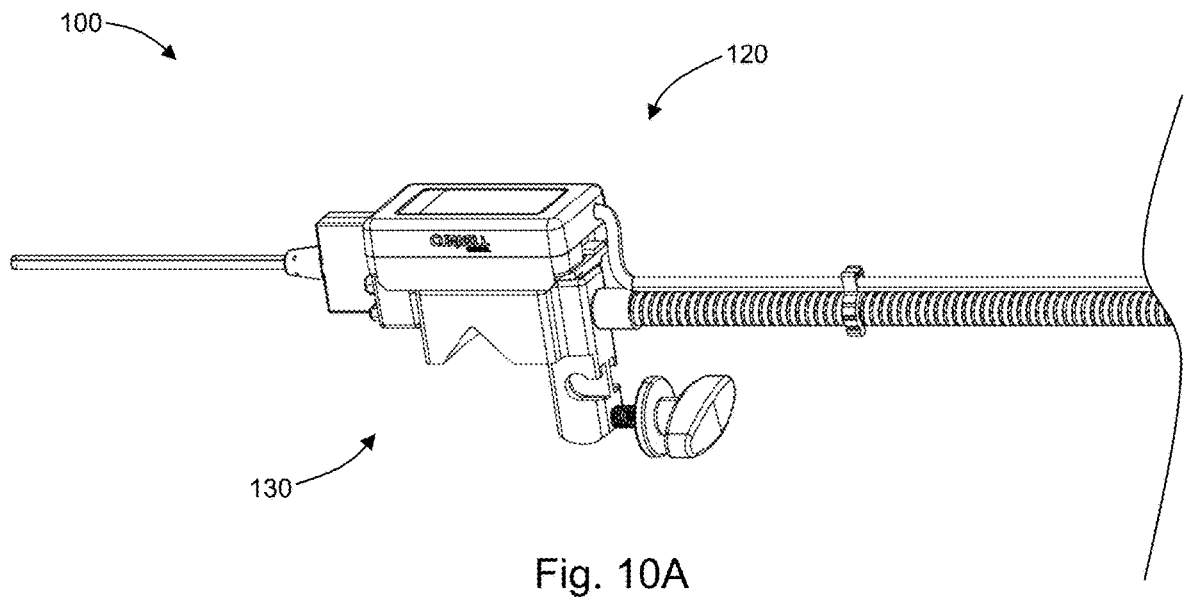
FIG. 10A shows a portion of another embodiment of a breath-operated interface device having a station interconnect with a single plug.
Figure 10B:
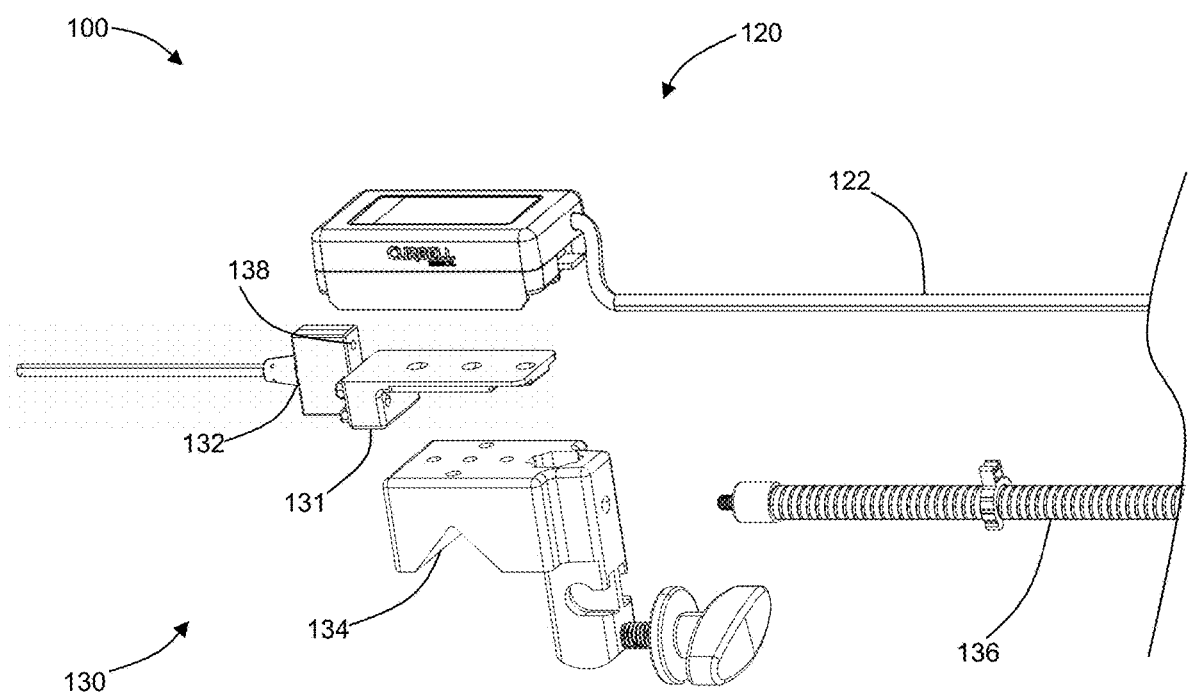
FIG. 10B is an exploded view of the device of FIG. 10A.

FIGS. 8, 10A, and 10B depict a portion of another embodiment of a breath-operated interface device 100 according to the present disclosure. The device 100 includes a disposable portion 120 with a breath tube 120. A base 130 is shown with a frame 131 and a station interconnect 132. A second signal coupler 138 is shown in the station interconnect 132. A clamp 134 (a portion of the clamp is shown) is attached to the frame 131. A gooseneck arm 136 is attached to the clamp 134. The embodiment depicted in FIG. 8 shows an interconnect 132 with a double plug. FIG. 9 shows an interconnect 133 configured with an 8-pin DIN connector.

In another aspect, the present disclosure may be embodied as a disposable module for a breath-operated interface device. The disposable module may be of any configuration shown or described herein and configured for attachment to a base. In such an embodiment, the base does not make up a portion of the device.

Figure 11:
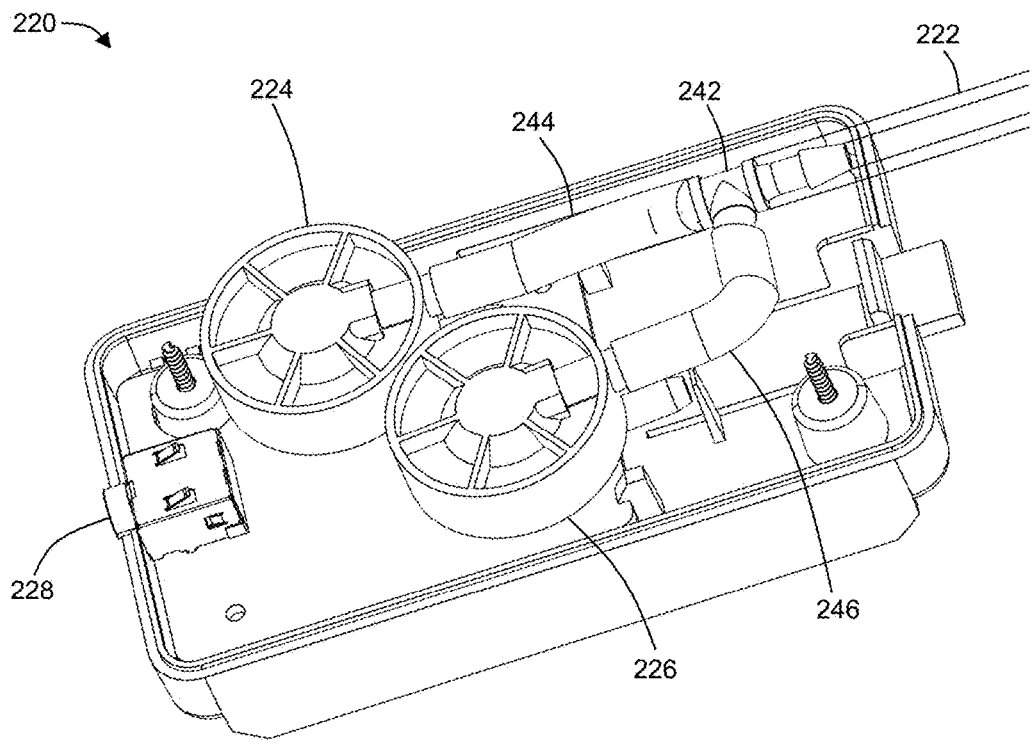
FIG. 11 is a view of a portion of a disposable module according to another embodiment of the present disclosure wherein a portion of the housing has been removed.

FIG. 11 depicts another embodiment of a disposable module 220 having a first pressure differential switch 224 and a second pressure differential switch 226. The first pressure differential switch 224 is in pneumatic communication with a breath tube 222 by way of a first branch tube 244 and Y-connector 242. The second pressure differential switch 226 is in pneumatic communication with the breath tube 222 by way of a second branch tube 246 and Y-connector 242. The disposable module 220 includes a first signal coupler 228 which is configured as a 3.5 mm jack (i.e., for connection with a corresponding 3.5 mm plug of a base). The first pressure differential switch 224 may be configured to be actuated by a user "puffing" into the breath tube 222 (pressure increase). The second pressure differential switch may be configured to be actuated by a user "sipping" into the breath tube 222 (vacuum—pressure decrease).

Figure 12:
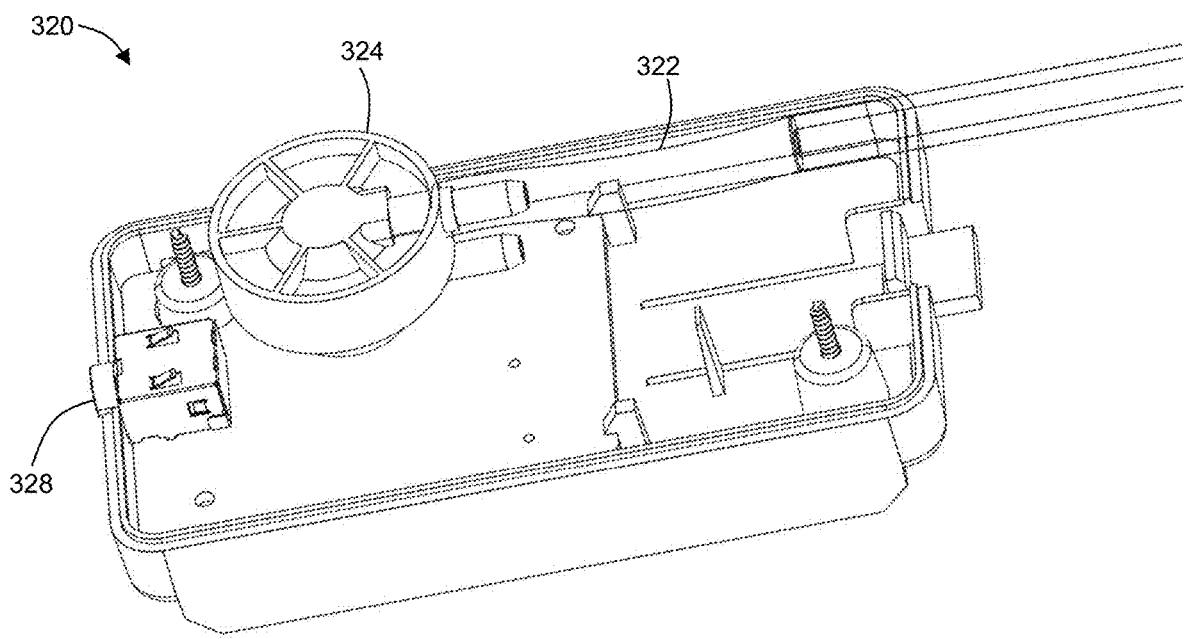
FIG. 12 is a view of a disposable module according to another embodiment of the present disclosure wherein a portion of the housing has been removed.

FIG. 12 depicts another embodiment of a disposable module 320 having a first pressure differential switch 324. The first pressure differential switch 224 is in pneumatic communication with a breath tube 322. The disposable module 320 includes a first signal coupler 328 which is configured as a 3.5 mm jack (i.e., for connection with a corresponding 3.5 mm plug of a base). The first pressure differential switch 324 may be configured to be actuated by a user "puffing" into the breath tube 322 (pressure increase). In other embodiments, the first pressure differential switch 324 may be configured to be actuated by a user "sipping" into the breath tube 322 (pressure decrease). In other embodiments, the first pressure differential switch 324 may be configured to be actuated in a first actuation state by a user "puffing" into the breath tube 322 (pressure increase) and also actuated in a second actuation state by a user "sipping" into the breath tube 322 (pressure decrease).

Devices according to the present disclosure allow disposable modules to be purchased separately (e.g., for each individual), while the base is reusable. The disposable module may be configured to removably attach from the base with using simple techniques which may not necessarily require tools. For example, the disposable module may attach to the base using a sliding, twisting, pressing motion, etc. or combinations. The disposable module may include additional components to prevent accidental removal from the base, such as, for example, magnetic components, latches, snaps, fasteners, etc. While embodiments may include additional components in the disposable module (e.g., signal circuits, etc.), it may be advantageous to limit the components included in the disposable module to only those which must be changed for each individual (e.g., for purposes of hygiene, avoiding cross-contamination, etc.)

Although the present disclosure has been described with respect to one or more particular embodiments, it will be understood that other embodiments of the present disclosure may be made without departing from the spirit and scope of the present disclosure.

We claim:

1. A breath-operated interface device, comprising:
    a disposable module, comprising:
        a breath tube having an inlet;
        a first pressure differential switch in pneumatic communication with the breath tube and configured to be actuated by a change in pressure in the breath tube;
        a first signal coupler in electrical communication with the first pressure differential switch to receive a signal according to an actuation state of the first pressure differential switch; and
    a base, comprising:
        a second signal coupler configured to detachably electrically connect with the first signal coupler of the disposable module; and
        a station interconnect configured to interface with an external system.

2. The device of claim 1, wherein the first pressure differential switch is configured to be actuated by an increase in pressure in the breath tube.

3. The device of claim 2, wherein the disposable module further comprises a second pressure differential switch in pneumatic communication with the breath tube and configured to be actuated by a decrease in pressure in the breath tube, and wherein the first signal coupler is in electrical communication with the second pressure differential switch to receive a signal according to an actuation state of the second pressure differential switch.

4. The device of claim 1, wherein the first pressure differential switch is configured to be actuated by a decrease in pressure in the breath tube.

5. The device of claim 1, wherein the first pressure differential switch has a first actuation state actuated by an increase in pressure in the breath tube and a second actuation state actuated by a decrease in pressure in the breath tube.

6. The device of claim 1, further comprising a body, and wherein the first pressure differential switch is mounted to the body.

7. The device of claim 6, wherein the body is a housing, and the first pressure differential switch is contained within the housing.

8. The device of claim 7, wherein at least a portion of the first signal coupler is external to the housing.

9. The device of claim 6, wherein the base is configured for removable attachment of the body of the disposable module.

10. The device of claim 1, wherein the first signal coupler is a 3.5 mm plug and the second coupler is a 3.5 mm jack.

11. The device of claim 1, wherein the base further comprises a clamp for attachment of the base to an object.

12. The device of claim 1, wherein the base further comprises an arm configured for attachment of the breath tube at one or more locations along a length of the arm.

13. The device of claim 1, wherein the station interconnect is configured to interface with a nurse call system.

14. The device of claim 13, wherein the station interconnect is configured to interface with the nurse call system via an 8-pin DIN connector, a "plug, a double ¾" plug, and/or an RJ45 connector.

15. The device of claim 1, wherein the station interconnect further comprises a signal circuit.

* * * * *